United States Patent
Nomura et al.

[19]

[11] Patent Number: 5,871,450
[45] Date of Patent: Feb. 16, 1999

[54] ANESTHETIC DEPTH MEASURING APPARATUS

[75] Inventors: Takashi Nomura; Hideichi Tsuda, both of Komaki, Japan

[73] Assignee: Colin Corporation, Aichi, Japan

[21] Appl. No.: 776,158

[22] PCT Filed: May 24, 1996

[86] PCT No.: PCT/JP96/01418

§ 371 Date: Jan. 27, 1997

§ 102(e) Date: Jan. 27, 1997

[87] PCT Pub. No.: WO96/38087

PCT Pub. Date: Dec. 5, 1996

[30]    Foreign Application Priority Data

Jun. 2, 1995  [JP]  Japan  .................................... 7-136947
Jun. 2, 1995  [JP]  Japan  .................................... 7-136948
Jun. 2, 1995  [JP]  Japan  .................................... 7-136949

[51] Int. Cl.$^6$ ........................................................ A61B 5/00
[52] U.S. Cl. ........................................ 600/485; 600/500
[58] Field of Search ................................ 600/485, 493–6, 600/500, 748

[56]              References Cited

U.S. PATENT DOCUMENTS

| 4,423,738 | 1/1984  | Newgard . |
| 4,533,346 | 8/1985  | Cosgrove, Jr. et al. ................ 600/544 |
| 4,788,982 | 12/1988 | Gedeon et al. ......................... 600/483 |
| 5,390,679 | 2/1995  | Martin et al. ........................... 600/486 |
| 5,632,272 | 5/1997  | Diab et al. ............................. 600/479 |

FOREIGN PATENT DOCUMENTS

| A2-0 050 983 | 5/1982  | European Pat. Off. . |
| A2-0 232 234 | 8/1987  | European Pat. Off. . |
| B2-3-67410   | 10/1991 | Japan . |
| A-4-371166   | 12/1992 | Japan . |
| A-5-253196   | 10/1993 | Japan . |
| WO 92/06632  | 4/1992  | WIPO . |

*Primary Examiner*—Robert L. Nasser
*Attorney, Agent, or Firm*—Oliff & Berridge, PLC

[57]              ABSTRACT

From a fluctuation of pulse periods of a subject continuously measured by a pulse period measuring device, a first pulse period fluctuation signal $HFC_{RR}$ which corresponds to a first pulse period fluctuation component produced in substantial synchronism with a respiration of the subject and a second pulse period fluctuation signal $LFC_{RR}$ which corresponds to a second pulse period fluctuation component having a predetermined frequency lower than a frequency of the first pulse period fluctuation component are extracted by a pulse period fluctuation signal extracting means. Then, based on a ratio ($HFC_{RR}/LFC_{RR}$) of the first pulse period fluctuation signal $HFC_{RR}$ to the second pulse period fluctuation signal $LFC_{RR}$, an anesthetic depth of the subject is calculated by an anesthetic depth calculating means. Thus, the present apparatus can objectively or quantitatively calculate the anesthetic depth of the subject. Additionally, the apparatus can accurately measure the anesthetic depth of the subject without needing operator's skill or the like.

4 Claims, 13 Drawing Sheets

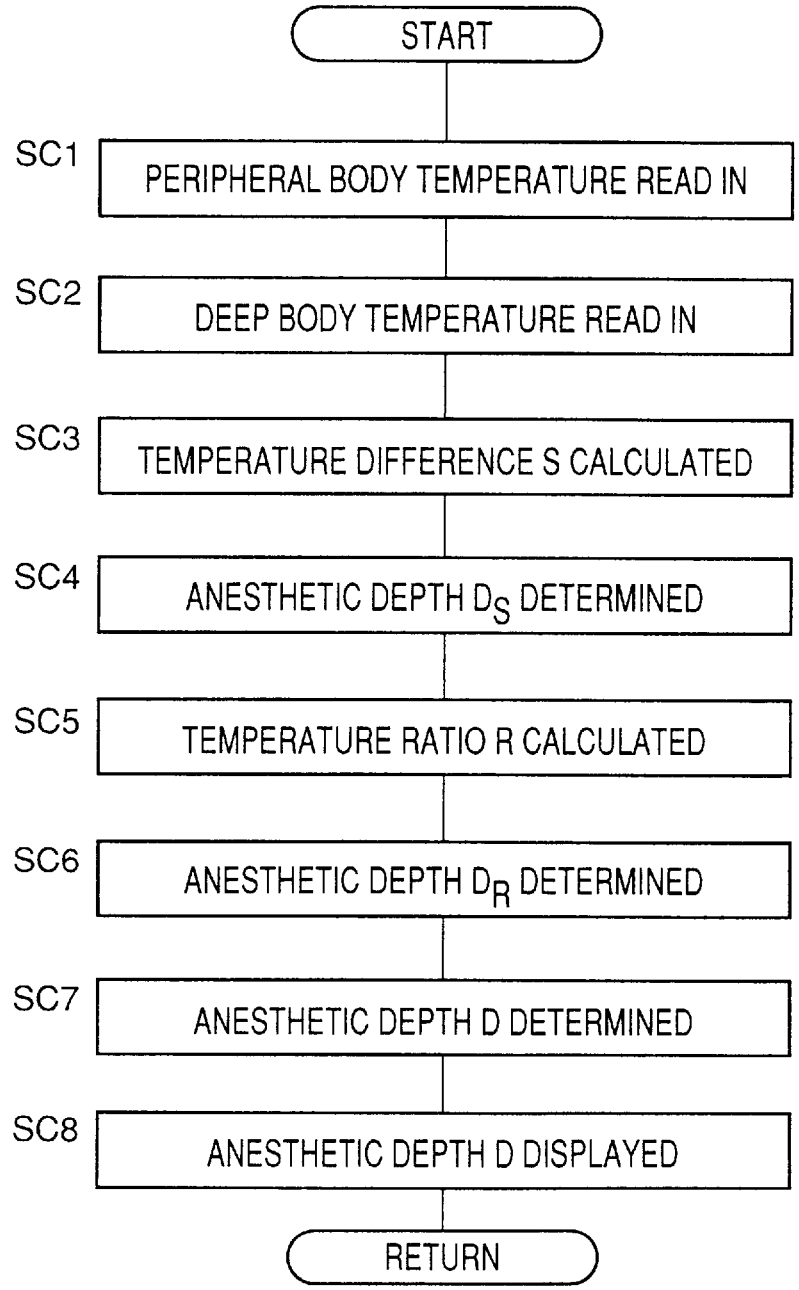

ANESTHETIC DEPTH MEASURING APPARATUS

FIELD OF THE ART

The present invention relates to an anesthetic depth measuring apparatus for measuring an anesthetic depth of a living subject.

BACKGROUND OF THE INVENTION

When a patient is anesthetized for a surgery or the like, it is required to maintain a suitable anesthetic depth so as to protect the patient from stress or pain due to the surgery. Conventionally, for example, an anesthetic depth has been subjectively or empirically recognized by monitoring a change of a blood pressure, a heart rate or a respiration rate of the patient, resulting from a stimulation of the surgery, or observing a reflex of eyelashes, a dimension of a pupil, a hue of a limb or a body temperature of the patient.

However, since the anesthetic depth recognition based on the change of the blood pressure, the heart rate or the respiration rate, or based on the reflex of the eyelashes, the dimension of the pupil, the hue of the limb or the body temperature is performed depending on a subjective judgement of anesthetists or the like, the anesthetists are required to have a long-time experience and a skill. In addition, it is not easy to objectively or accurately recognize the anesthetic depth. It is therefore an object of the present invention to provide an anesthetic depth measuring apparatus for objectively measuring an anesthetic depth of a living subject.

The inventors of the present invention have continued their study in the background of the above described situation, and they have found that a magnitude of a pulse period fluctuation component produced in synchronism with a respiration of a subject, a magnitude of a blood pressure fluctuation component having a frequency lower than a frequency of the respiration of the subject or a rate of change of the pulse period to the blood pressure of the subject has a close relation to an activity level of subject's parasympathetic nerve or sympathetic nerve, whereby an anesthetic depth of the subject can be objectively measured on the basis of the magnitude of the above mentioned fluctuation component, when the subject is anesthetized.

Moreover, the present inventors have found that the influences of the anesthesia on a peripheral body temperature and a deep body temperature are different from each other, and a difference between the peripheral body temperature and the deep body temperature has a close relation to an activity level of a nerve of the subject, whereby an anesthetic depth of the subject can be objectively measured on the basis of the difference. The present invention has been developed based on those findings.

DISCLOSURE OF THE INVENTION

The above object may be achieved according to the first invention which provides an anesthetic depth measuring apparatus for measuring an anesthetic depth of a living subject, characterized by comprising: (a) a pulse period measuring device which continuously measures a period of a pulse of the subject; (b) pulse period fluctuation signal extracting means for extracting, from a fluctuation of the pulse periods continuously measured by the pulse period measuring device, a first pulse period fluctuation signal which corresponds to a first pulse period fluctuation component produced in substantial synchronism with a respiration of the subject and a second pulse period fluctuation signal which corresponds to a second pulse period fluctuation component having a predetermined frequency lower than a frequency of the first pulse period fluctuation component; and (c) anesthetic depth calculating means for calculating an anesthetic depth of the subject based on a ratio of the first pulse period fluctuation signal to the second pulse period fluctuation signal.

In the above mentioned apparatus, from a fluctuation of the pulse periods continuously measured by the pulse period measuring device, the first pulse period fluctuation signal which corresponds to the first pulse period fluctuation component produced in substantial synchronism with the respiration of the subject and the second pulse period fluctuation signal which corresponds to the second pulse period fluctuation component having a predetermined frequency lower than a frequency of the first pulse period fluctuation component are extracted by the pulse period fluctuation signal extracting means. Then, based on a ratio of the first pulse period fluctuation signal to the second pulse period fluctuation signal, the anesthetic depth of the subject is calculated by the anesthetic depth calculating means. Thus, the present apparatus can objectively or quantitatively calculate the anesthetic depth of the subject. Additionally, the apparatus can accurately measure the anesthetic depth without needing operator's skill or the like.

The above object may be achieved according to the second invention which provides an anesthetic depth measuring apparatus for measuring an anesthetic depth of a living subject, characterized by comprising: (a) a blood pressure measuring device which continuously measures a blood pressure value of the subject; (b) blood pressure fluctuation signal extracting means for extracting, from a fluctuation of the blood pressure values continuously measured by the blood pressure measuring device, a blood pressure fluctuation signal which corresponds to a blood pressure fluctuation component having a predetermined frequency lower than a frequency of a respiration of the subject; and (c) anesthetic depth calculating means for calculating an anesthetic depth of the subject based on a magnitude of the blood pressure fluctuation signal.

In the above mentioned apparatus, the blood pressure value of the subject is continuously measured by the blood pressure measuring device, and, from a fluctuation of the continuously measured blood pressure values, the blood pressure fluctuation signal which corresponds to the blood pressure fluctuation component having a predetermined frequency lower than a frequency of the respiration of the subject is extracted by the blood pressure fluctuation signal extracting means. Then, based on a magnitude of the blood pressure fluctuation signal, the anesthetic depth of the subject is calculated by the anesthetic depth calculating means. Thus, the present apparatus can objectively or quantitatively calculate the anesthetic depth of the subject. Additionally, the apparatus can accurately measure the anesthetic depth without needing operator's skill or the like.

The above object may be achieved according to the third invention which provides an anesthetic depth measuring apparatus for measuring an anesthetic depth of a living subject, characterized by comprising: (a) a pulse period measuring device which continuously measures a period of a pulse of the subject; (b) a blood pressure measuring device which continuously measures a blood pressure value of the subject; (c) change rate calculating means for calculating a rate of change of one of the blood pressure values continuously measured by the blood pressure measuring device and the pulse periods continuously measured by the pulse period measuring device, to the other of the blood pressure values and the pulse periods; and (d) anesthetic depth determining means for determining an anesthetic depth of the subject based on the rate of change calculated by the change rate calculating means.

In the above mentioned apparatus, the pulse period of the subject is continuously measured by the pulse period measuring device, the blood pressure value of the subject is continuously measured by the blood pressure measuring device, and a rate of change of one of the blood pressure values and the pulse periods to the other of the blood pressure values and the pulse periods is calculated by the change rate calculating means. Then, based on the rate of change, the anesthetic depth of the subject is determined by the anesthetic depth determining means. Thus, the present apparatus can objectively or quantitatively determine the anesthetic depth of the subject. Additionally, the apparatus can accurately measure the anesthetic depth without needing operator's skill or the like.

The above object may be achieved according to the fourth invention which provides an anesthetic depth measuring apparatus for measuring an anesthetic depth of a living subject, characterized by comprising: (a) a peripheral body temperature measuring device which measures a peripheral body temperature of the subject; (b) a deep body temperature measuring device which measures a deep body temperature of the subject; (c) temperature difference calculating means for calculating a difference between the peripheral body temperature measured by the peripheral body temperature measuring device and the deep body temperature measured by the deep body temperature measuring device; and (d) anesthetic depth determining means for determining an anesthetic depth of the subject based on the difference calculated by the temperature difference calculating means.

In the above mentioned apparatus, the difference between the peripheral body temperature measured by the peripheral body temperature measuring device and the deep body temperature measured by the deep body temperature measuring device is calculated by the temperature difference calculating means. Then, based on the difference calculated by the temperature difference calculating means, the anesthetic depth of the subject is determined by the anesthetic depth determining means. Thus, the present apparatus can objectively or quantitatively determine the anesthetic depth of the subject. Additionally, the apparatus can accurately calculate the anesthetic depth without needing operator's skill or the like.

The above object may be achieved according to the fifth invention which provides an anesthetic depth measuring apparatus for measuring an anesthetic depth of a living subject, characterized by comprising: (a) a peripheral body temperature measuring device which measures a peripheral body temperature of the subject; (b) a deep body temperature measuring device which measures a deep body temperature of the subject; (c) temperature ratio calculating means for calculating a ratio of the peripheral body temperature measured by the peripheral body temperature measuring device to the deep body temperature measured by the deep body temperature measuring device; and (d) anesthetic depth determining means for determining an anesthetic depth of the subject based on the ratio calculated by the temperature ratio calculating means.

In the above mentioned apparatus, the ratio of the peripheral body temperature measured by the peripheral body temperature measuring device to the deep body temperature measured by the deep body temperature measuring device is calculated by the temperature ratio calculating means. Then, based on the ratio calculated by the temperature ratio calculating means, the anesthetic depth of the subject is determined by the anesthetic depth determining means. Thus, the present apparatus can objectively or quantitatively determine the anesthetic depth of the subject. Additionally, the apparatus can accurately measure the anesthetic depth without needing operator's skill or the like.

BRIEF DESCRIPTION OF THE DRAWINGS

FIG. 17 is a flow chart representing the operation of the control device of the apparatus of FIG. 13.

THE BEST MODE FOR CARRYING OUT THE INVENTION

Figure 1:
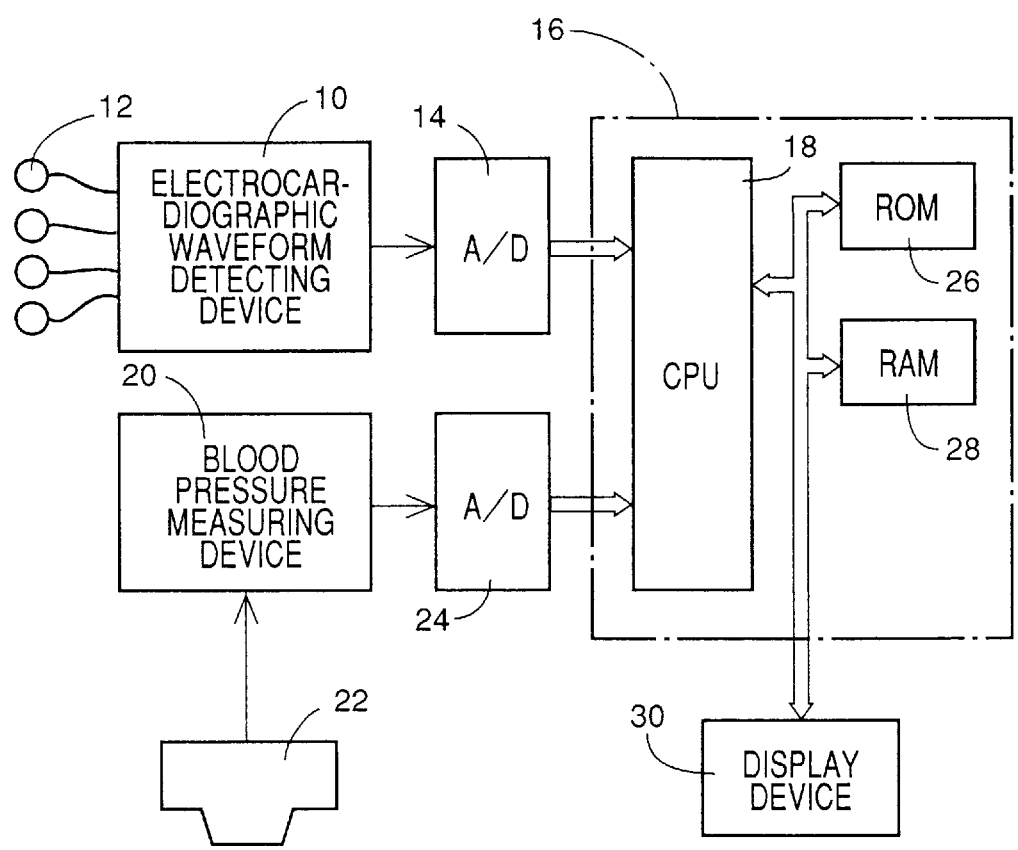
FIG. 1 is a diagrammatic view for illustrating the construction of an anesthetic depth measuring apparatus embodying the present invention.

There will be described in detail an embodiment of the present invention, referring to the drawings.

FIG. 1 is a diagrammatic view for illustrating the construction of an anesthetic depth measuring apparatus embodying the present invention. In the figure, an electrocardiographic waveform detecting device 10 includes a plurality of electrodes 12 which are put on a living subject. The device 10 continuously supplies a well-known electrocardiographic waveform signal successively produced in synchronism with a heartbeat of the subject who is generally anesthetized by an inhalation anesthetic, such as isoflurane, to a CPU 18 of a control device 16 via an A/D converter 14.

A blood pressure measuring device 20 includes a pressure pulse wave detecting probe 22 adapted to be pressed, with a band (not shown), to an artery of the subject, such as a carotid artery, a radial artery or a pedal dorsal artery. The device 20 continuously measures a blood pressure value of the generally anesthetized subject based on each one pulse of the detected pulse wave and supplies a blood pressure signal representative of the blood pressure value to the CPU 18 of the control device 16 via an A/D converter 24. This blood pressure measuring device 20 is constructed similarly to the blood pressure monitoring apparatus disclosed in U.S. Pat. No. 4,423,738 or laid-open publication No. 5-253196 of unexamined Japanese Patent Application.

The control device 16 is provided by a so-called microcomputer including the CPU 18, a ROM 26 and a RAM 28. The CPU 18 processes input signals, that is, the electrocardiographic waveform signal and the blood pressure signal, according to control programs pre-stored in the ROM 26 by utilizing a temporary-storage function of the RAM 28, and controls a display device 30 so as to display an anesthetic depth D of the subject.

Figure 2:
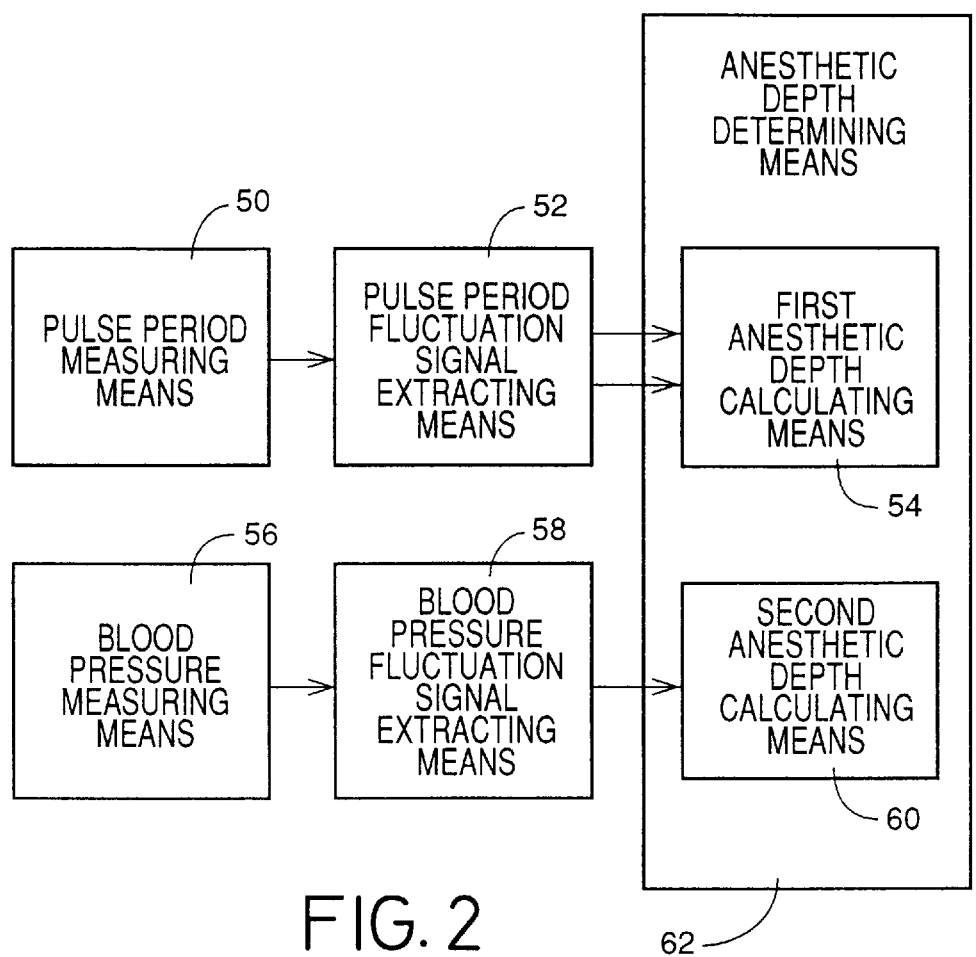
FIG. 2 is a block diagram for explaining various functions of a control device of the apparatus of FIG. 1.
Figure 3:
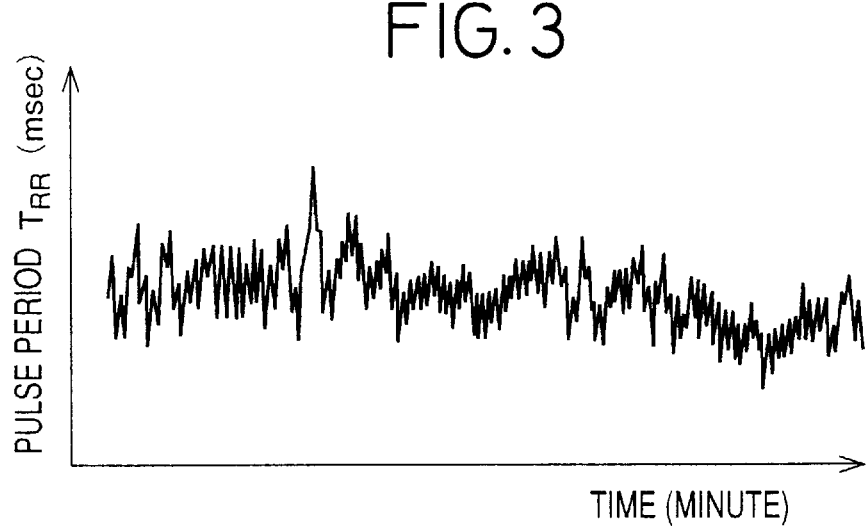
FIG. 3 is a view for illustrating a fluctuation of pulse periods $T_{RR}$ measured by the apparatus of FIG. 1.

FIG. 2 is a block diagram for explaining various functions of the control device 16. In the figure, a pulse period measuring means 50 measures a pulse period from a heartbeat synchronous wave, such as an electrocardiographic waveform, a pulse wave produced from an artery, or the like, produced in synchronism with a heartbeat of the subject. Preferably, by calculating a time interval between each pair of successive two pulses of the electrocardiographic waveform, for example, R-waves of the successive two pulses, the pulse period measuring means 50 continuously measures a pulse period $T_{RR}$ of the anesthetized subject. The thus measured pulse periods $T_{RR}$ have a fluctuation as shown in FIG. 3, for example.

Figure 4:
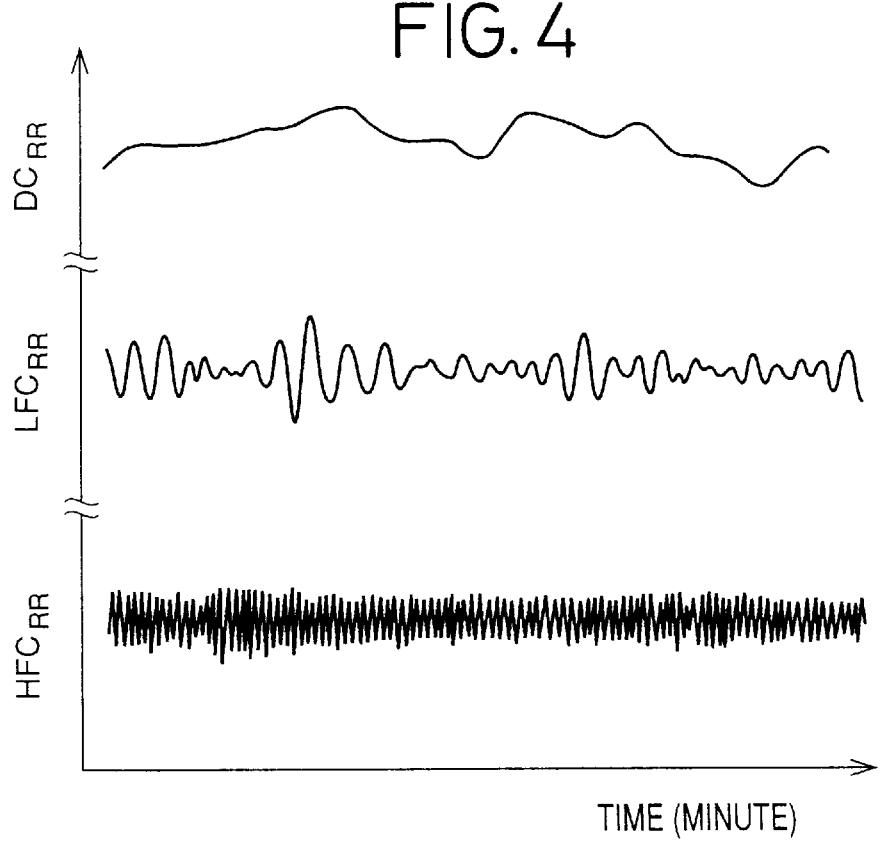
FIG. 4 is a view for illustrating a first pulse period fluctuation signal $HFC_{RR}$, a second pulse period fluctuation signal $LFC_{RR}$ and a pulse period direct current component $DC_{RR}$ which are extracted from the fluctuation of the pulse periods $T_{RR}$ measured by the apparatus of FIG. 1.

A pulse period fluctuation signal extracting means 52 extracts, from the fluctuation of the pulse periods $T_{RR}$ continuously measured by the pulse period measuring means 50, a first pulse period fluctuation signal $HFC_{RR}$ which corresponds to a first pulse period fluctuation component produced in substantial synchronism with a respiration of the subject and a second pulse period fluctuation signal $LFC_{RR}$ which corresponds to a second pulse period fluctuation component having a predetermined frequency lower than a frequency of the first pulse period fluctuation component. The pulse period fluctuation signal extracting means 52 performs a frequency analysis of the fluctuation of the pulse periods $T_{RR}$, with a fast Fourier transformation (FFT) method, an autoregression (AR) method, or the like. Then, the pulse period fluctuation signal extracting means 52 outputs, as the first and second pulse period fluctuation signals $HFC_{RR}$, $LFC_{RR}$, a magnitude (power) of a signal component having a frequency in the neighborhood of the frequency of the respiration of the subject and a magnitude (power) of a signal component having a frequency in the neighborhood of one third to one fourth of the frequency of the respiration of the subject, respectively. Specifically, the pulse period fluctuation signal extracting means 52 outputs, as the first and second pulse period fluctuation signals $HFC_{RR}$, $LFC_{RR}$, a magnitude of a signal component having a peak frequency in a predetermined frequency range including a frequency (e.g., 0.25 Hz) of the respiration of the subject and a magnitude of a signal component having a peak frequency in a predetermined frequency range including a frequency (e.g., 0.07 Hz) of about one third to one fourth of the frequency of the respiration of the subject, respectively. FIG. 4 respectively illustrates respective magnitudes of the first and second pulse period fluctuation signals $HFC_{RR}$, $LFC_{RR}$ and a 0 Hz frequency component (direct current component) signal $DC_{RR}$ which are extracted from the fluctuation of the pulse periods $T_{RR}$.

A first anesthetic depth calculating means 54 included in an anesthetic depth determining means 62 calculates a first anesthetic depth $D_{RR}$ of the subject based on a ratio ($LFC_{RR}/HFC_{RR}$) of the first pulse period fluctuation signal $HFC_{RR}$ to the second pulse period fluctuation signal $LFC_{RR}$ which are extracted by the pulse period fluctuation signal extracting means 52. The first anesthetic depth calculating means 54 calculates the first anesthetic depth $D_{RR}$ based on the actual ratio ($LFC_{RR}/HFC_{RR}$) according to a pre-stored relationship shown in FIG. 5, for example.

Figure 5:
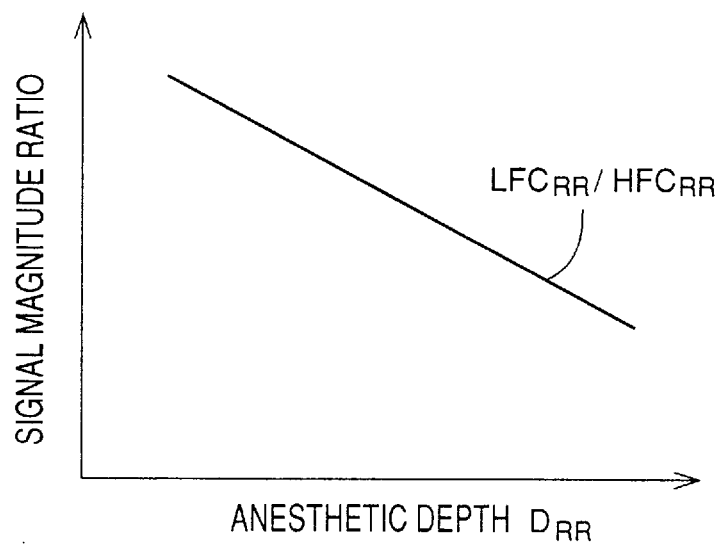
FIG. 5 is a graph showing a relationship used by the apparatus of FIG. 1 for calculating an anesthetic depth $D_{RR}$.

It is speculated that, in the action of a cardiac vagus nerve that is an efferent nerve originating from a circulatory center, a respiratory fluctuation occurs due to the interference of a respiratory center with the circulatory center at the level of a brain stem and a respiratory fluctuation of afferent signals produced from cardio-pulmonary receptors. Therefore, a fluctuation appearing in a frequency of ignition of a sinoauricular node can be regarded as a magnitude (power) of a signal component having a peak frequency in a frequency range including a frequency (e.g., 0.25 Hz) of the respiration of the subject, that is, the first pulse period fluctuation signal $HFC_{RR}$. Moreover, the respiratory fluctuation occurs to the action of a sympathetic nerve which controls the sinoauricular node. However, since the pulse rate control under the sympathetic nerve has a characteristic as a low frequency range filter, the sympathetic nerve can transmit only pulse rate fluctuations having extremely low frequencies, e.g., frequencies not higher than 0.15 Hz, and $HFC_{RR}$ having an ordinary respiration frequency is exclusively mediated by the vagus nerve. Thus, the amplitude of $HFC_{RR}$, that is, magnitude of $HFC_{RR}$ is in proportion to the activity of the cardiac vagus nerve and may be used as a useful and quantitative index of the cardiac vagus nerve activity. Meanwhile, it is speculated that the second pulse period fluctuation signal $LFC_{RR}$ corresponding to a fluctuation component having a frequency of about one third to one fourth of a frequency of the first pulse period fluctuation signal $HFC_{RR}$ is caused by a pulse rate fluctuation which occurs via a baroreceptor reflex mechanism. Afferent and efferent nerves of the reflex are an aortic sinus nerve, and cardiac parasympathetic and sympathetic nerves, respectively. Since the signal $LFC_{RR}$ is in proportion to a product of the amplitude of the blood pressure and the sensitivity of the baroreceptors, the sympathetic nerve activity cannot be evaluated, if the baroreceptor reflex sensitivity is not constant. Thus, the ratio ($LFC_{RR}/HFC_{RR}$) closely corresponds to the nerve activity, because of being freed from an influence of an individual difference. The relationship shown in FIG. 5 is experimentally obtained in advance, based on the above described facts.

A blood pressure measuring means 56 which is provided by, for example, the blood pressure measuring device 20, continuously measures a blood pressure value of the subject. A blood pressure fluctuation signal extracting means 58 extracts, from a fluctuation of the blood pressure values, for example, systolic blood pressure values $P_{SYS}$, continuously measured by the blood pressure measuring means 56, a blood pressure fluctuation signal $LFC_{SYS}$ which corresponds to a blood pressure fluctuation component having a predetermined frequency lower than the frequency of the respiration of the subject. The blood pressure fluctuation signal extracting means 58 performs a frequency analysis of the fluctuation of the blood pressure values $P_{SYS}$, with a fast Fourier transformation (FFT) method, an autoregression (AR) method, or the like, and outputs, as the blood pressure fluctuation signal $LFC_{SYS}$, a magnitude (power) of a signal component having a peak frequency in a frequency range including a frequency (e.g., 0.07 Hz) of about one third to one fourth of the frequency of the respiration of the subject.

Figure 6:
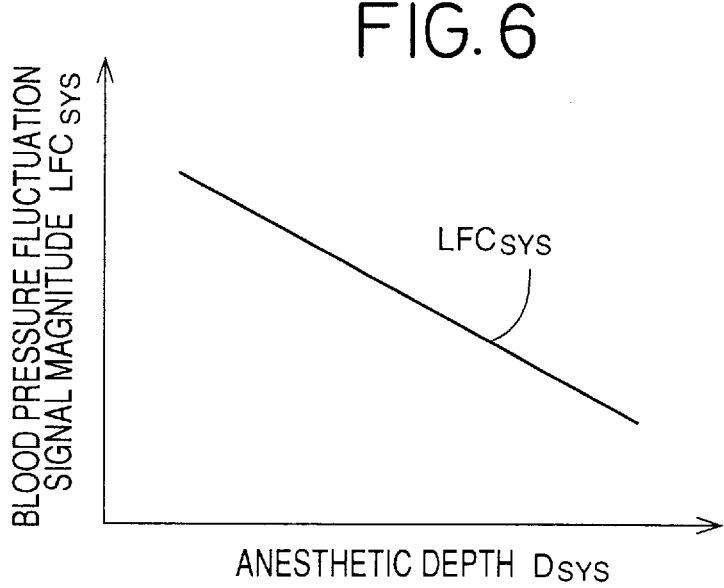
FIG. 6 is a graph showing a relationship used by the apparatus of FIG. 1 for calculating an anesthetic depth $D_{SYS}$.

A second anesthetic depth calculating means 60 included in the anesthetic depth determining means 62 calculates a second anesthetic depth $D_{SYS}$ of the subject based on a magnitude of the blood pressure fluctuation signal $LFC_{SYS}$ according to a pre-stored relationship as shown in FIG. 6, for example. Since it is speculated that the blood pressure fluctuation signal $LFC_{SYS}$ representative of the fluctuation of blood pressure values results from a delay of a sympathetic vasomotor regulation system, an amplitude (magnitude) of the signal $LFC_{SYS}$ may be used as a quantitative index of a vasomotor sympathetic nerve activity. A relationship shown in FIG. 6 is experimentally obtained in advance, based on the above described facts.

The anesthetic depth determining means 62 determines a third anesthetic depth D based on the first anesthetic depth $D_{RR}$ calculated by the first anesthetic depth calculating means 54 and the second anesthetic depth $D_{SYS}$ calculated by the second anesthetic depth calculating means 60. For example, if the first and second anesthetic depths $D_{RR}$, $D_{SYS}$ are extremely different from each other, the anesthetic depth determining means 62 judges, based on respective time-wise changes of the two anesthetic depths, which one of the two anesthetic depths $D_{RR}$ and $D_{SYS}$ is abnormal, and determines, as the third anesthetic depth D, the other of the anesthetic depths $D_{RR}$ and $D_{SYS}$, or calculates respective weighing factors based on the respective time-wise changes of the two anesthetic depths and determines, as the third anesthetic depth D, an average value of the respective weighed values of the anesthetic depths $D_{RR}$ and $D_{SYS}$. Meanwhile, if the first and second anesthetic depths $D_{RR}$, $D_{SYS}$ are not so different from each other, the anesthetic depth determining means 62 determines, as the third anesthetic depth D, one of the two anesthetic depths $D_{RR}$, $D_{SYS}$, or an average value of the two anesthetic depths $D_{RR}$ and $D_{SYS}$.

Figure 7:
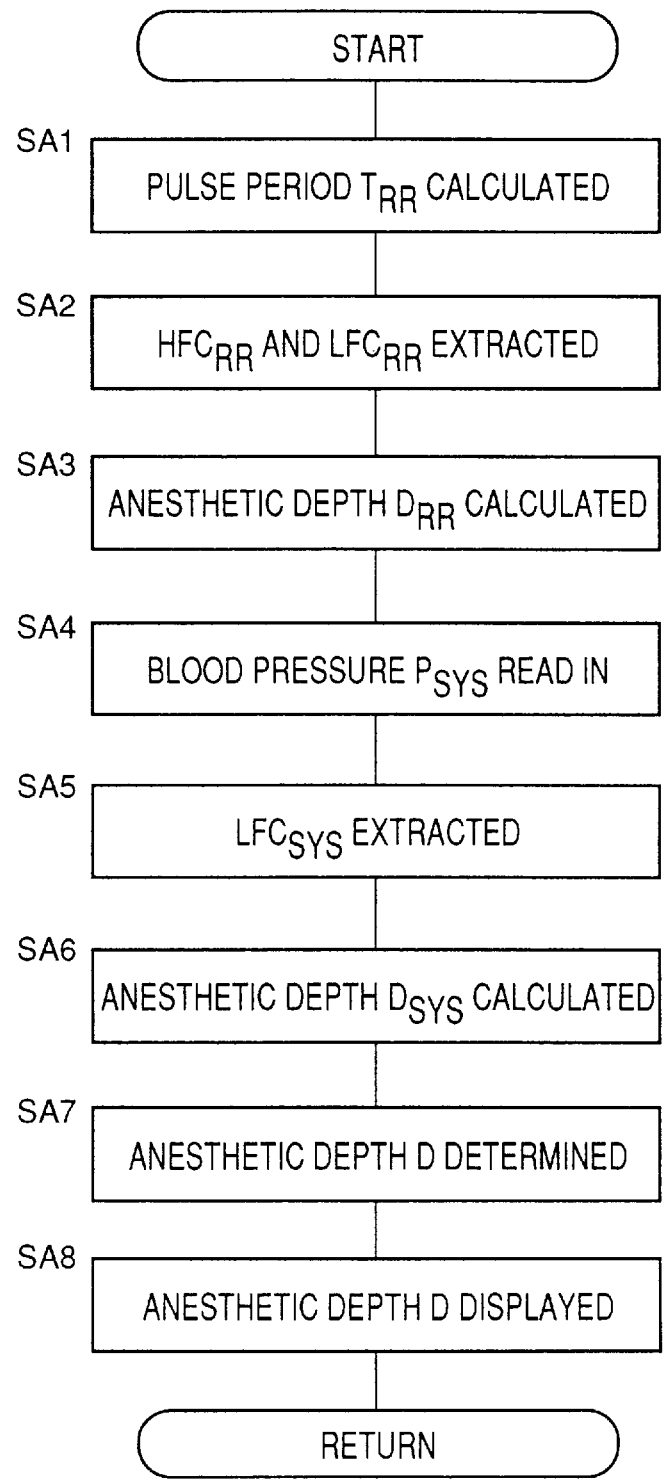
FIG. 7 is a flow chart representing the operation of the control device of the apparatus of FIG. 1.

FIG. 7 is a flow chart representing the operation of the control device 16, which shows a routine carried out in synchronism with a pulse or an input of a blood pressure value.

In FIG. 7, at Step SA1 corresponding to the pulse period measuring means 50, a pulse period $T_{RR}$ is calculated as a time interval between respective R-waves of successive two pulses of the electrocardiographic waveform input from the electrocardiographic waveform detecting device 10. Step SA1 is followed by Step SA2, corresponding to the pulse period fluctuation signal extracting means 52, to perform a frequency analysis of a fluctuation of the pulse periods $T_{RR}$ with a fast Fourier transformation (FFT) method, an autoregression (AR) method, or the like, and extract, as first and second pulse period fluctuation signals $HFC_{RR}$, $LFC_{RR}$, a magnitude (power) of a signal component having a peak frequency in a frequency range including a frequency (e.g., 0.25 Hz) of a respiration of the subject and a magnitude (power) of a signal component having a peak frequency in a frequency range including a frequency (e.g., 0.07 Hz) of about one third to one fourth of the frequency of the respiration of the subject, respectively.

Step SA2 is followed by Step SA3, corresponding to the first anesthetic calculating means 54, to calculate a first anesthetic depth $D_{RR}$ of the subject based on a ratio ($LFC_{RR}/HFC_{RR}$) of the first pulse period fluctuation signal $HFC_{RR}$ to the second pulse period fluctuation signal $LFC_{RR}$ according to the pre-stored relationship shown in FIG. 5, for example.

Next, the control of the CPU 18 goes to Step SA4. At Step SA4, a blood pressure value $P_{SYS}$ input from the blood pressure measuring device 20 is read in. Step SA4 is followed by Step SA5, corresponding to the blood pressure fluctuation signal extracting means 58, to perform a frequency analysis of a fluctuation of the blood pressure values $P_{SYS}$, with a fast Fourier transformation (FFT) method, an autoregression (AR) method, or the like, and extract, as the blood pressure fluctuation signal $LFC_{SYS}$, a magnitude (power) of a signal component having a peak frequency in a frequency range including a frequency (e.g., 0.07 Hz) of about one third to one fourth of the frequency of the respiration of the subject.

Step SA5 is followed by Step SA6, corresponding to the second anesthetic depth calculating means 60, to calculate a second anesthetic depth $D_{SYS}$ of the subject based on the blood pressure fluctuation signal $LFC_{SYS}$ extracted at Step SA5 according to the pre-stored relationship shown in FIG. 6, for example.

Subsequently, the control of the CPU 18 goes to Step SA7, corresponding to the anesthetic depth determining means 62, to determine a third anesthetic depth D having a higher reliability, based on the first anesthetic depth $D_{RR}$ calculated on the basis of the fluctuation of pulse periods and the second anesthetic depth $D_{SYS}$ calculated on the basis of the fluctuation of blood pressure values. For example, if the first and second anesthetic depths $D_{RR}$, $D_{SYS}$ are extremely different from each other, one of the first and second anesthetic depths $D_{RR}$, $D_{SYS}$ is judged as an abnormal value, based on respective time-wise changes of the two anesthetic depths, and the other of the first and second anesthetic depths $D_{RR}$, $D_{SYS}$ is determined as the third anesthetic depth D. If the first and second anesthetic depths $D_{RR}$, $D_{SYS}$ are not so different from each other, an average value of the first and second anesthetic depths $D_{RR}$, $D_{SYS}$ is determined as the third anesthetic depth D. Step SA7 is followed by Step SA8 to quantitatively display, on the display device 30, the anesthetic depth D determined at Step SA7, in digits, a trend graph, or the like. For instance, the anesthetic depth D is expressed with numerals by dividing the axis of abscissas of FIG. 5 or 6 into predetermined units.

In the above described embodiment, from the fluctuation of the pulse periods continuously measured at Step SA1 corresponding to the pulse period measuring means 50, the first pulse period fluctuation signal $HFC_{RR}$ which corresponds to the first pulse period fluctuation component produced in substantial synchronism with the respiration of the subject and the second pulse period fluctuation signal $LFC_{RR}$ which corresponds to the second pulse period fluctuation component having the predetermined frequency lower than the frequency of the first pulse period fluctuation component are extracted at Step SA2 corresponding to the pulse period fluctuation signal extracting means 52. Then, the first anesthetic depth $D_{RR}$ of the subject is calculated at Step SA3 corresponding to the first anesthetic depth calculating means 54, based on the ratio ($LFC_{RR}/HFC_{RR}$) of the first pulse period fluctuation signal $HFC_{RR}$ to the second pulse period fluctuation signal $LFC_{RR}$. Thus, the present apparatus can objectively or quantitatively calculate the first anesthetic depth $D_{RR}$ of the subject and accurately obtain the anesthetic depth $D_{RR}$ without needing operator's skill or the like.

In the present embodiment, the blood pressure values $P_{SYS}$ of the subject are continuously measured by the blood pressure measuring means 56. From the fluctuation of the continuously measured blood pressure values $P_{SYS}$, the blood pressure fluctuation signal $LFC_{SYS}$ which corresponds to the blood pressure fluctuation component having the predetermined frequency lower than the frequency of the respiration of the subject is extracted at Step SA5 corresponding to the blood pressure fluctuation signal extracting means 58. Then, the second anesthetic depth $D_{SYS}$ of the subject is calculated at Step SA6 corresponding to the second anesthetic depth calculating means 60, based on the magnitude of the blood pressure fluctuation signal $LFC_{SYS}$. Thus, the present apparatus can objectively or quantitatively calculate the second anesthetic depth $D_{SYS}$ of the subject and accurately obtain the anesthetic depth $D_{SYS}$ without needing operator's skill or the like.

In the present embodiment, based on the first anesthetic depth $D_{RR}$ calculated on the basis of the fluctuation of pulse periods $T_{RR}$ and the second anesthetic depth $D_{SYS}$ on the basis of the fluctuation of blood pressure values $P_{SYS}$, the third anesthetic depth D having a higher reliability is determined at Step SA7 corresponding to the anesthetic depth determining means 62, whereby the anesthetic depth D quantitatively displayed on the display device 30 enjoys the higher reliability.

Next, there will be described another embodiment according to the present invention. Hereinafter, the same parts as those of the prior embodiment are denoted by the same reference numerals and the detail description thereof is omitted.

Figure 8:
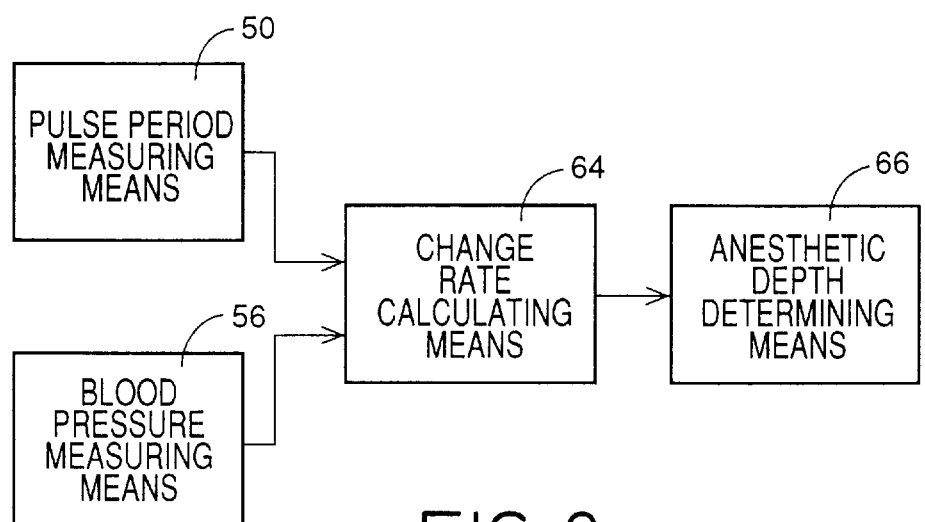
FIG. 8 is a block diagram corresponding to FIG. 2, for explaining various functions of a control device of an anesthetic depth measuring apparatus as another embodiment according to the present invention.

FIG. 8 is a block diagram for explaining various functions of the control device 16 of an anesthetic depth measuring apparatus as another embodiment according to the present invention. In the figure, a change rate calculating means 64 calculates a rate of change, $\Delta T_{RR}/\Delta P_{SYS}$, of a pulse period $T_{RR}$ to a blood pressure value $P_{SYS}$, based on the blood pressure values, for example, systolic blood pressure values $P_{SYS}$ continuously measured by the blood pressure measuring means 56 and the pulse periods $T_{RR}$ measured by the pulse period measuring means 50, within a predetermined unit time which corresponds to, for example, ten pulses to several tens of pulses. For example, the rate of change $\Delta T_{RR}/\Delta P_{SYS}$ is calculated as a slope or inclination of a regression line determined on data points indicating actual blood pressure values $P_{SYS}$ and actual pulse periods $T_{RR}$ of the subject in a two-dimensional coordinate system defined by a first axis indicative of blood pressure values $P_{SYS}$ and a second axis indicative of pulse periods $T_{RR}$.

Figure 9:
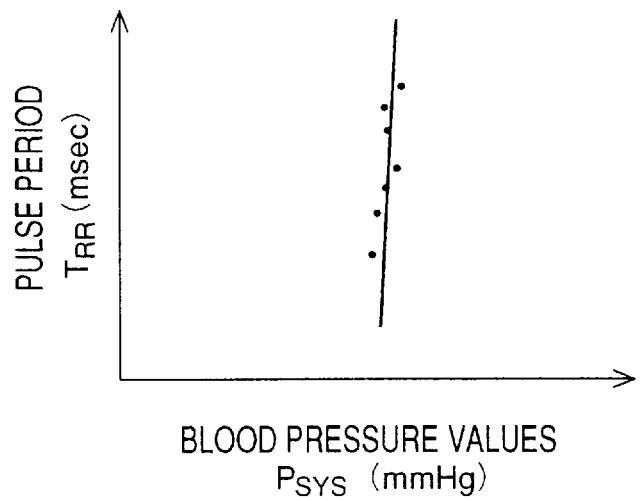
FIG. 9 is a graph showing a relationship between pulse periods $T_{RR}$ and blood pressure values $P_{SYS}$ of a non-anesthetized subject.
Figure 10:
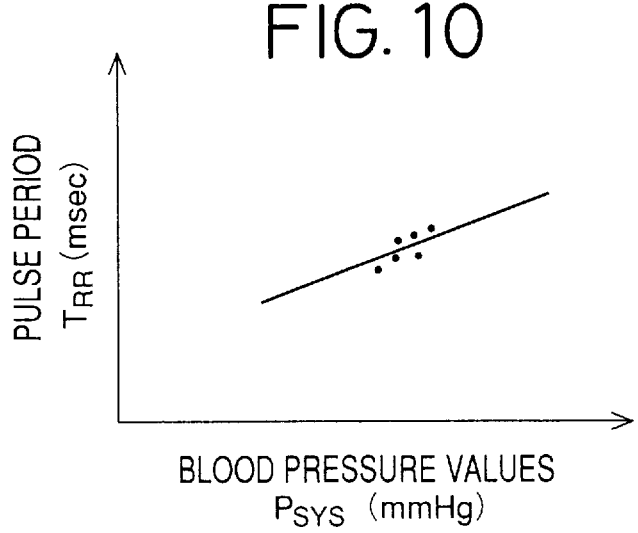
FIG. 10 is a graph showing a relationship between pulse periods $T_{RR}$ and blood pressure values $P_{SYS}$ of an anesthetized subject.

When each data point indicative of an actual blood pressure value $P_{SYS}$ and an actual pulse period $T_{RR}$ of the anesthetized subject is plotted in the two-dimensional coordinate system defined by the first axis indicative of blood pressure values $P_{SYS}$ and the second axis indicative of pulse periods $T_{RR}$, eventually those data points are located along a straight line. Thus, the blood pressure values and the pulse periods are related to each other. The rate of change $\Delta T_{RR}/\Delta P_{SYS}$ indicates the inclination of the straight line. When the subject is not anesthetized, the inclination of the straight line indicates a large value as shown in FIG. 9, for example. When the subject is anesthetized, the inclination of the straight line indicates a small value as shown in FIG. 10, for example. As one of nerve-based circulation control mechanisms, there is known a baroreceptor reflex which acts via an automatic nerve. The baroreceptor reflex causes an effector organ such as the heart, peripheral blood vessels, or the like to adjust heart rate or arterial pressure so as to eliminate changes of the blood pressure and keep the blood pressure constant. Further, the baroreceptor reflex not only reacts to changes of blood vessels due to a physiological stress, a postural change or a bleeding, but also is influenced by an anesthetic agent. Therefore, the rate of change $\Delta T_{RR}/\Delta P_{SYS}$ changes according to the anesthetic depth. A relationship shown in FIG. 11 is experimentally obtained in advance, based on the above described facts.

Figure 11:
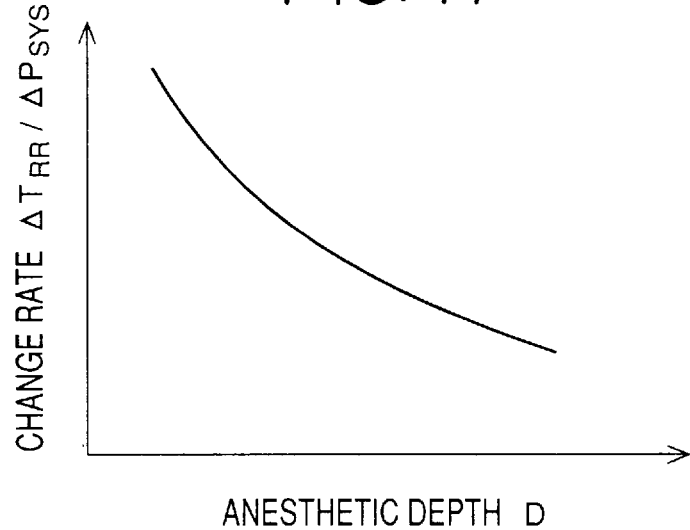
FIG. 11 is a graph showing a relationship used by the apparatus of FIG. 8 for determining an anesthetic depth D based on a rate of change $\Delta T_{RR}/\Delta P_{SYS}$.

An anesthetic depth determining means 66 determines an anesthetic depth D of the subject based on the rate of change $\Delta T_{RR}/\Delta P_{SYS}$ calculated by the change rate calculating means 64 according to the pre-stored relationship shown in FIG. 11.

Figure 12:
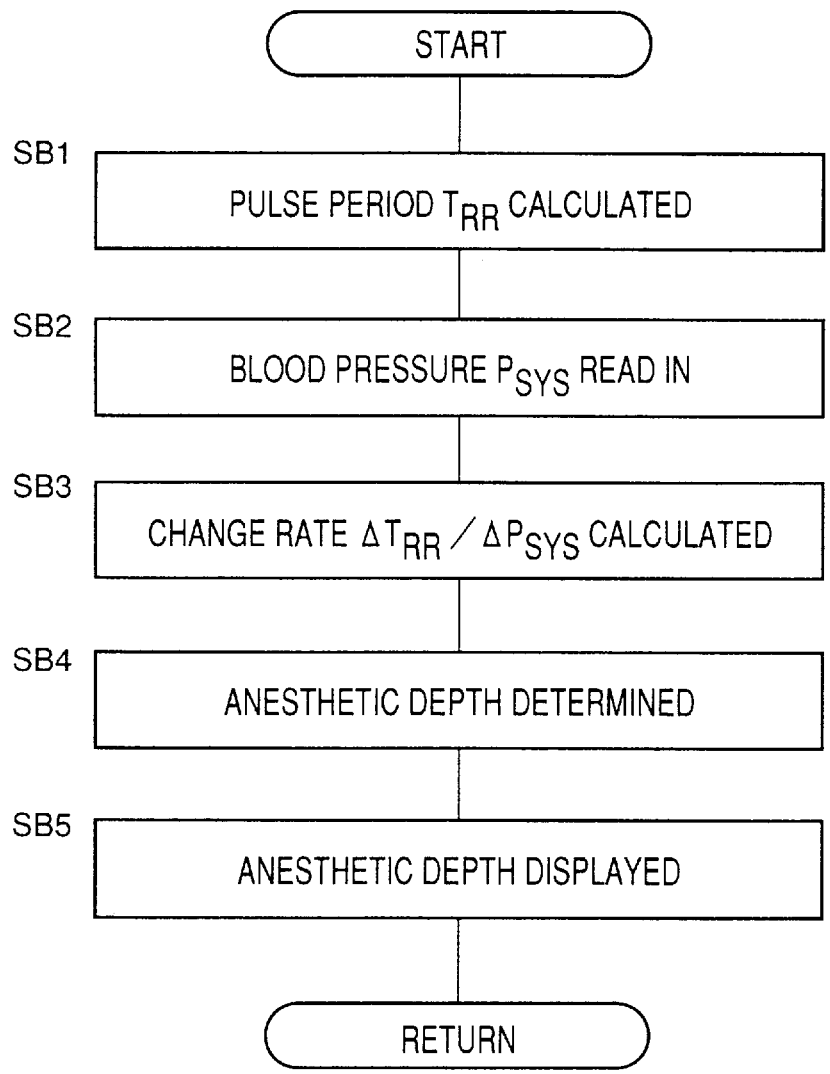
FIG. 12 is a flow chart representing the operation of the control device of the apparatus of FIG. 8.

FIG. 12 is a flow chart representing the operation of the control device 16 of the second apparatus, which shows a routine carried out in synchronism with a pulse or an input of a blood pressure value, or at a predetermined regular time interval or a predetermined unit of pulses.

In FIG. 12, at Step SB1 corresponding to the pulse period measuring means 50, a pulse period $T_{RR}$ is calculated as a time interval between respective R-waves of successive two pulses of the electrocardiographic waveform input from the electrocardiographic waveform detecting device 10. Step SB1 is followed by Step SB2 to read in, for example, a systolic blood pressure value $P_{SYS}$ measured by the blood pressure measuring device 20 corresponding to the blood pressure measuring means 56.

Step SB2 is followed by Step SB3, corresponding to the change rate calculating means 64, to calculate a rate of change $\Delta T_{RR}/\Delta P_{SYS}$ as an inclination of a regression line obtained from a plurality of data points each indicating an actual blood pressure value $P_{SYS}$ and an actual pulse period $T_{RR}$ of the subject that are plotted in a two-dimensional coordinate system defined by a first axis indicative of blood pressure values $P_{SYS}$ and a second axis indicative of pulse periods $T_{RR}$.

Subsequently, the control of the CPU 18 goes to Step SB4, corresponding to the anesthetic depth determining means 66, to determine an anesthetic depth D of the subject based on the rate of change $\Delta T_{RR}/\Delta P_{SYS}$ calculated at Step SB3 according to the pre-stored relationship shown in FIG. 11, for example. Step SB4 is followed by Step SB5 to display, on the display device 30, the determined anesthetic depth D in digits, a trend graph, or the like.

In the above mentioned embodiment, the rate of change $\Delta T_{RR}/\Delta P_{SYS}$ is calculated at Step SB3 corresponding to the change rate calculating means 64, based on the pulse periods $T_{RR}$ continuously measured at Step SB1 corresponding to the pulse period measuring means 50 and the blood pressure values $P_{SYS}$ continuously measured by the blood pressure measuring means 56. Then, the anesthetic depth D is determined at Step SB4 corresponding to the anesthetic depth determining means 66, based on the rate of change $\Delta T_{RR}/\Delta P_{SYS}$ according to the relationship shown in FIG. 11. Thus, the second apparatus can objectively and quantitatively determine the anesthetic depth D of the subject and accurately obtain the anesthetic depth D without needing operator's skill or the like.

Figure 13:
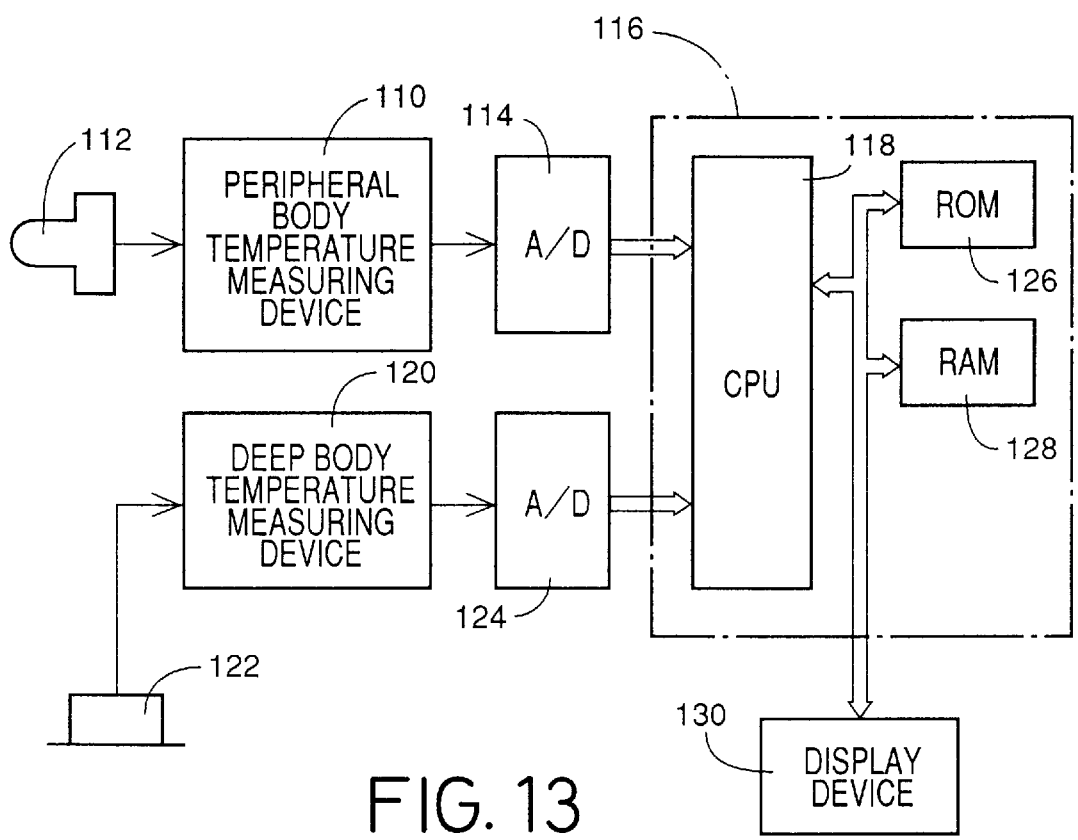
FIG. 13 is a diagrammatic view for illustrating the construction of an anesthetic depth measuring apparatus as yet another embodiment according to the present invention.

FIG. 13 is a diagrammatic view for illustrating the construction of an anesthetic depth measuring apparatus as yet another embodiment according to the present invention. In the figure, a peripheral body temperature measuring device 110 includes a peripheral body temperature measuring probe 112 which is worn on a living subject. The peripheral body temperature measuring device 110 measures a peripheral body temperature of the subject who is generally anesthetized by an inhalation anesthetic, such as isoflurane, and successively supplies a peripheral body temperature signal representative of the measured peripheral body temperature to a CPU 118 of a control device 116 via an A/D converter 114. The peripheral body temperature measuring probe 112 includes a thermistor, for example, and is adhered to a skin of the subject, such as a forehead or a sole.

A deep body temperature measuring device 120 includes a deep body temperature measuring probe 122 which is worn on the subject. The deep body temperature measuring device 120 measures a deep body temperature, that is, a central body temperature of the generally anesthetized subject, and successively supplies a deep body temperature signal representative of the measured deep body temperature to the CPU 118 via an A/D converter 124. The deep body temperature measuring probe 122 is constructed such that a temperature sensor portion thereof is insulated by a thermal insulator so that the sensor portion is brought into equilibrium with the deep body temperature of the subject. Otherwise, the deep body temperature measuring probe 122 may be provided by an insertion-type probe which is inserted into a rectum or an esophagus and measures a deep body temperature of a living the subject.

The control device 116 is provided by a so-called microcomputer including the CPU 118, a ROM 126 and a RAM 128. The CPU 118 processes input signals, that is, the peripheral body temperature signal and the deep body temperature signal, according to control programs pre-stored in the ROM 126 by utilizing a temporary-storage function of the RAM 128, and controls a display device 130 to display an anesthetic depth D of the subject.

Figure 14:
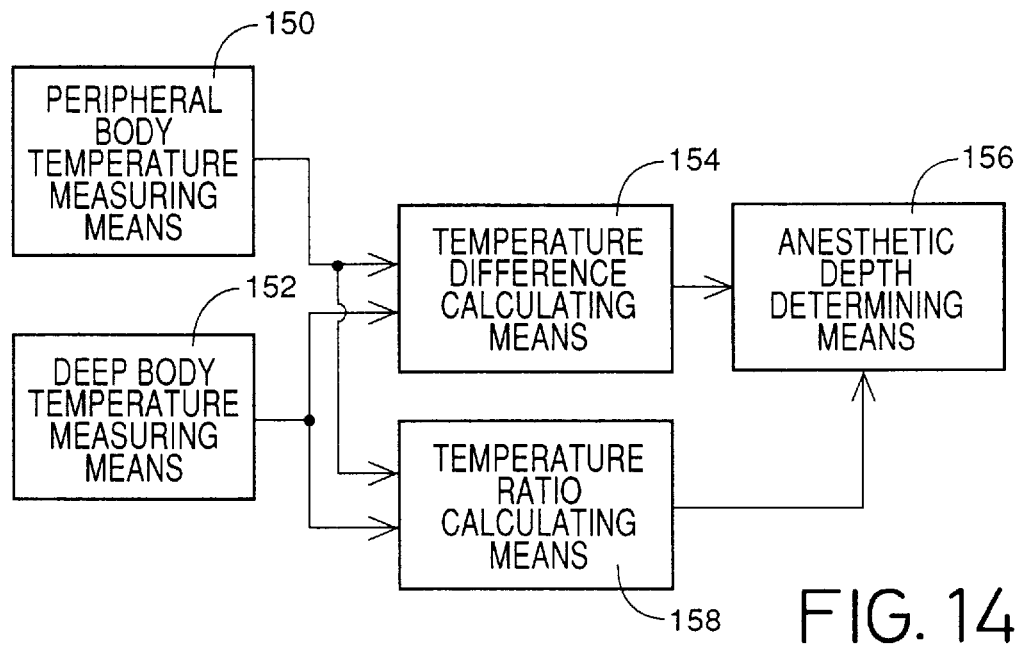
FIG. 14 is a block diagram for explaining various functions of a control device of the apparatus of FIG. 13.

FIG. 14 is a block diagram for explaining various functions of the control device 116. In the figure, a peripheral body temperature measuring means 150 corresponds to the peripheral body temperature measuring device 110 and measures a peripheral body temperature on a body surface of the subject. A deep body temperature measuring means 152 corresponds to the deep body temperature measuring device 120 and measures a deep body temperature in a central (deep) portion of the subject.

A temperature difference calculating means 154 calculates a difference S ($=T_{cent}-T_{dist}$) between the peripheral body temperature $T_{dist}$ measured by the peripheral body temperature measuring means 150 and the deep body temperature $T_{cent}$ measured by the deep body temperature measuring means 152. An anesthetic depth determining means 156 determines an anesthetic depth $D_S$ based on the actual difference S according to a pre-stored relationship shown in FIG. 15, for example.

Meanwhile, a temperature ratio calculating means 158 calculates a ratio R ($T_{cent}/T_{dist}$) of the peripheral body temperature $T_{dist}$ measured by the peripheral body temperature measuring means 150 to the deep body temperature $T_{cent}$ measured by the deep body temperature measuring means 152. The anesthetic depth determining means 156 determines an anesthetic depth $D_R$ based on the actual ratio R according to a pre-stored relationship shown in FIG. 16, for example. Further, the anesthetic depth determining means 156 determines a more reliable anesthetic depth D from the anesthetic depth $D_S$ determined based on the difference S and the anesthetic depth $D_R$ determined based on the ratio R.

Figure 15:
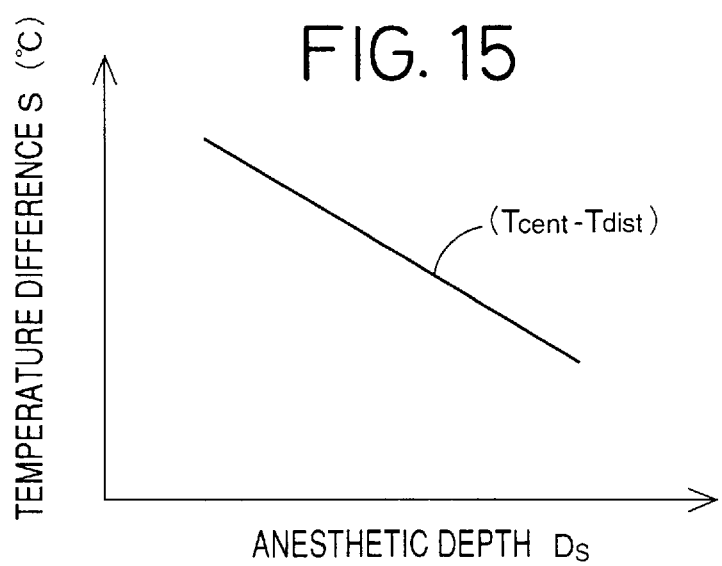
FIG. 15 is a graph showing a relationship used by the apparatus of FIG. 13 for determining an anesthetic depth $D_S$ based on a temperature difference S $(=T_{cent}-T_{dist})$.
Figure 16:
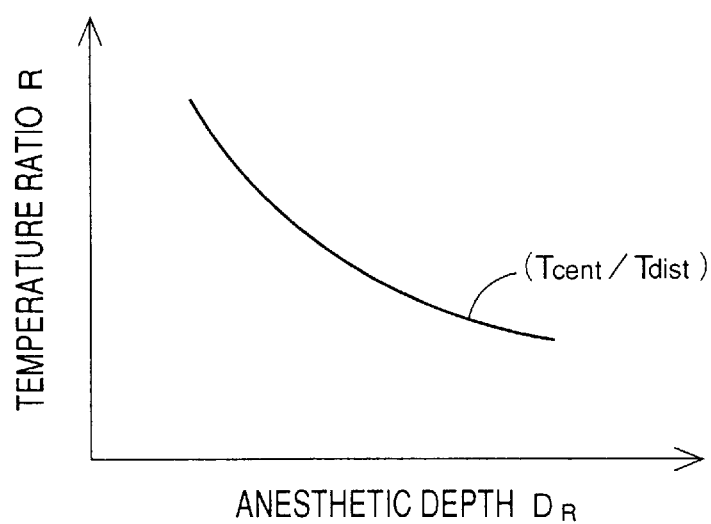
FIG. 16 is a graph showing a relationship used by the apparatus of FIG. 13 for determining an anesthetic depth $D_R$ based on a temperature ratio R $(=T_{cent}/T_{dist})$.

Generally, blood vessels of an anesthetized patient tend to be relaxed and dilated. In this case, blood circulation of subject's peripheral portion is promoted and the peripheral body temperature $T_{dist}$ is raised. Therefore, as the difference S ($=T_{cent}-T_{dist}$) between the peripheral body temperature $T_{dist}$ and the deep body temperature (central temperature) $T_{cent}$ or the ratio R ($=T_{cent}/T_{dist}$) of the central body temperature $T_{cent}$ to the peripheral body temperature $T_{dist}$ decreases, an anesthetic effect increases and the anesthetic depth D increases. The relationships shown in FIGS. 15 and 16 are experimentally obtained in advance, based on the above described facts.

FIG. 17 is a flow chart representing the operation of the control device 116, which shows a routine carried out in synchronism with an input of a peripheral or a deep body temperature $T_{dist}$, $T_{cent}$.

In FIG. 17, at Step SC1, a peripheral body temperature $T_{dist}$ measured by the peripheral body temperature measuring device 110 is read in. Step SC1 is followed by Step SC2 to read in a deep body temperature $T_{cent}$ measured by the deep body temperature measuring device 120. Step SC2 is followed by Step SC3, corresponding to the temperature difference calculating means 154, to calculate a difference S ($=T_{cent}-T_{dist}$) between the deep body temperature $T_{cent}$ and the peripheral body temperature $T_{dist}$. Step SC3 is followed by Step SC4, corresponding to the anesthetic depth determining means 156, to determine an anesthetic depth $D_S$ based on the actual difference S ($=T_{cent}-T_{dist}$) according to the pre-stored relationship shown in FIG. 15.

Subsequently, the control of the CPU 118 goes to Step SC5, corresponding to the temperature ratio calculating means 158. At Step SC5, a ratio R ($=T_{cent}/T_{dist}$) of the central body temperature $T_{cent}$ to the peripheral body temperature $T_{dist}$ is calculated. Step SC5 is followed by Step SC6, corresponding to the anesthetic depth determining means 156, to determine an anesthetic depth $D_R$ based on the actual ratio R ($=T_{cent}/T_{dist}$) according to the pre-stored relationship shown in FIG. 16.

Step SC6 is followed by Step SC7, corresponding to the anesthetic depth determining means 156, to determine a more reliable anesthetic depth D based on the anesthetic depths $D_S$ and $D_R$ determined on the basis of the difference S ($=T_{cent}-T_{dist}$) and the ratio R ($=T_{cent}/T_{dist}$), respectively. For example, if the two anesthetic depths $D_S$ and $D_R$ are extremely different from each other, one of the two anesthetic depths is judged as an abnormal value, based on respective time-wise changes of the two anesthetic depth, and the other of the two anesthetic depths is determined as the anesthetic depth D. If the two anesthetic depths $D_S$ and $D_R$ are not so different from each other, an average value of the two anesthetic depths is determined as the anesthetic depth D.

Step SC7 is followed by Step SC8 to quantitatively display, on the display device 130, the anesthetic depth D determined at Step SC7 in digits, a trend graph, or the like. For instance, the anesthetic depth D is expressed with numerals by dividing the axis of abscissas of FIG. 15 or 16 into predetermined units.

In the above mentioned embodiment, at Step SC3 corresponding to the temperature difference calculating means 154, the difference S ($=T_{cent}-T_{dist}$) between the deep body temperature $T_{cent}$ measured by the deep body temperature measuring means 152 and the peripheral body temperature $T_{dist}$ measured by the peripheral body temperature measuring means 150 is calculated. At Step SC4 corresponding to the anesthetic depth determining means 156, the anesthetic depth $D_S$ of the subject is determined on the basis of the difference S ($=T_{cent}-T_{dist}$). Thus, the present apparatus can to objectively or quantitatively determine the anesthetic depth $D_S$ of the subject and accurately obtain the anesthetic depth $D_S$ without needing operator's skill or the like.

Further, in the present embodiment, at Step SC5 corresponding to the temperature ratio calculating means 158, the ratio R ($=T_{cent}/T_{dist}$) of the central body temperature $T_{cent}$ measured by the deep body temperature measuring means 152 to the peripheral body temperature $T_{dist}$ measured by the peripheral body temperature measuring means 150 is calculated. At Step SC6 corresponding to the anesthetic depth determining means 156, the anesthetic depth $D_R$ of the subject is determined on the basis of the ratio R ($=T_{cent}/T_{dist}$) calculated by the temperature ratio calculating means 158. Thus, the present apparatus can objectively or quantitatively determine the anesthetic depth $D_S$ of the subject and accurately obtain the anesthetic depth $D_S$ without needing operator's skill or the like.

In the present embodiment, at Step SC7 corresponding to the anesthetic depth determining means 156, the anesthetic depth D having a higher reliability is determined, based on the anesthetic depth $D_S$ determined on the basis of the temperature difference S ($=T_{cent}-T_{dist}$) and the anesthetic depth $D_R$ determined on the basis of the temperature ratio R ($=T_{cent}/T_{dist}$), whereby the anesthetic depth D quantitatively displayed on the display device 130 enjoys the high reliability.

While the present invention has been described in its preferred embodiments by reference to the drawings, it is to be understood that the invention may otherwise be embodied.

In the embodiment shown in FIG. 2, both the means 50, 52, 54 for calculating the first anesthetic depth $D_{RR}$ from the fluctuation of the pulse periods $T_{RR}$, and the means 56, 58, 60 for calculating the second anesthetic depth $D_{SYS}$ from the fluctuation of the blood pressure values $P_{SYS}$ are employed. However, even if one of the two means for calculating the first and second anesthetic depths $D_{RR}$, $D_{SYS}$ is omitted, the apparatus can have the function of measuring an anesthetic depth.

Moreover, in the embodiment of FIG. 2, the pulse period $T_{RR}$ of the subject is continuously measured by calculating a period of an electrocardiographic waveform (ECG) detected by the electrocardiographic waveform detecting device 10, for example, calculating a time interval between respective R-waves of each pair of successive two pulses of the electrocardiographic waveform. However, it is possible to employ a means for pulse-synchronously calculating a period of a pulse wave detected by a well-known cuff or pressure pulse wave sensor from an artery of a living subject, or a means for pulse-synchronously calculating a period of a volume pulse wave detected by a photoelectric pulse wave sensor. In short, any kind of means for continuously measuring a pulse period of the subject may be provided. For example, when a pulse period is measured on the basis of the pressure pulse wave detected by the pressure pulse wave detecting probe 22 of the blood pressure measuring device 20, the electrocardiographic detecting device 10 is not needed.

In the embodiment shown in FIG. 2, as the pulse period $T_{RR}$, the blood pressure value $P_{SYS}$, or the anesthetic depth $D_{RR}$ or $D_{SYS}$, a moving average of values pulse-synchronously obtained within a predetermined period may be used. Further, the pulse period $T_{RR}$ or the blood pressure value $P_{SYS}$ may be obtained based on every second or third pulse.

In the embodiment shown in FIG. 2, the pulse period fluctuation signal extracting means 52 or the blood pressure fluctuation signal extracting means 58 may be provided by a digital filter for discriminating a micro-oscillation signal having a low frequency.

In the embodiment shown in FIG. 2, for the anesthetic depth $D_{SYS}$ calculation, the fluctuation of the systolic blood pressure values $P_{SYS}$ measured by the blood pressure measuring means 56 are used. However, a fluctuation of mean blood pressure values $P_{MEAN}$ or diastolic blood pressure values $P_{DIA}$ measured by the blood pressure measuring means 56 may be used.

In the embodiment shown in FIG. 2, the first and second pulse period fluctuation signals $HFC_{RR}$, $LFC_{RR}$ are obtained from the pulse periods $T_{RR}$ continuously measured by the pulse period measuring means 50. However, since the pulse period $T_{RR}$ (sec.) corresponds to a pulse rate PR ($=60/T_{RR}$), one to one, a means for measuring a pulse rate PR may be employed in place of the pulse period measuring means 50, and, from a fluctuation of the pulse rates PR, a first pulse rate fluctuation signal corresponding to a respiratory fluctuation and a second pulse rate fluctuation signal corresponding to one third to one fourth of the respiratory fluctuation may obtained.

In the embodiment shown in FIG. 2, the first anesthetic depth $D_{RR}$ of the subject is calculated on the basis of the ratio ($LFC_{RR}/HFC_{RR}$) of the second pulse period fluctuation signal $LFC_{RR}$ to the first pulse period fluctuation signal $HFC_{RR}$ and the second anesthetic depth $D_{SYS}$ is calculated on the basis of the magnitude of the blood pressure fluctuation signal $LFC_{SYS}$. However, the ratio ($LFC_{RR}/HFC_{RR}$) or the blood pressure fluctuation signal $LFC_{SYS}$ may be corrected or modified based on other parameters. In any case, the first anesthetic depth $D_{RR}$ of the subject is calculated on the basis of the ratio ($LFC_{RR}/HFC_{RR}$) of the second pulse period fluctuation signal $LFC_{RR}$ to the first pulse period fluctuation signal $HFC_{RR}$ and the second anesthetic depth $D_{SYS}$ is calculated on the basis of the magnitude of the blood pressure fluctuation signal $LFC_{SYS}$.

In the embodiment shown in FIG. 8, the rate of change $\Delta T_{RR}/\Delta P_{SYS}$ of the pulse period $T_{RR}$ to the blood pressure value $P_{SYS}$ is calculated and the anesthetic depth D is calculated on the basis of the rate of change $\Delta T_{RR}/\Delta P_{SYS}$. However, a rate of change $\Delta P_{SYS}/\Delta T_{RR}$ of the blood pressure value $P_{SYS}$ to the pulse period $T_{RR}$ may be used. The rate of change $\Delta P_{SYS}/\Delta T_{RR}$ increases with increasing of the anesthetic depth D.

In the embodiment shown in FIG. 8, the pulse period $T_{RR}$ is used. However, a heart rate HR may be used. Since the pulse period $T_{RR}$ is the inverse of the heart rate HR, a rate of change of the heart rate HR to the blood pressure value $P_{SYS}$ can be regarded as substantially the same as the rate of change $\Delta T_{RR}/\Delta P_{SYS}$.

In the embodiment shown in FIG. 8, the pulse period $T_{RR}$ and the blood pressure value $P_{SYS}$ are measured corresponding to each one pulse. However, the pulse period $T_{RR}$ and the blood pressure value $P_{SYS}$ may be measured at a predetermined regular interval which corresponds to two or more pulses. In addition, the pulse period $T_{RR}$ and the blood pressure value $P_{SYS}$ may be measured during an operation period which is started and ended at a predetermined cycle.

In the embodiment shown in FIG. 8, the pulse period $T_{RR}$ of the subject is continuously measured by calculating a period of an electrocardiographic waveform (ECG) detected by the electrocardiographic waveform detecting device 10, for example, calculating a time interval between respective R-waves of each pair of successive two pulses of the electrocardiographic waveform. However, it is possible to employ a means for pulse-synchronously calculating a period of a pulse wave detected by a well-known cuff or pressure pulse wave sensor from an artery of a living subject, or a means for pulse-synchronously calculating a period of a volume pulse wave detected by a photoelectric pulse wave sensor. In short, any kind of means for continuously measuring a pulse period of the subject may be provided. For example, when a pulse period is measured on the basis of the pressure pulse wave detected by the pressure pulse wave detecting probe 22 of the blood pressure measuring device 20, the electrocardiographic detecting device 10 is not needed.

In the embodiment shown in FIG. 8, the systolic blood pressure values $P_{SYS}$ measured by the blood pressure measuring device 20 are used. However, the mean blood pressure values $P_{MEAN}$ or the diastolic blood pressure values $P_{DIA}$ may be used.

In the embodiment shown in FIG. 8, as the pulse period $T_{RR}$ or the blood pressure value $P_{SYS}$, a moving average of values pulse-synchronously obtained within a predetermined duration may be used.

In the embodiment shown in FIG. 8, the anesthetic depth D is determined on the basis of the rate of change $\Delta T_{RR}/\Delta P_{SYS}$. However, the rate of change $\Delta T_{RR}/\Delta P_{SYS}$ may be corrected or modified based on other parameters. In any case, the anesthetic depth D is determined on the basis of the rate of change $\Delta T_{RR}/\Delta P_{SYS}$.

In the embodiment shown in FIG. 13, both the means 154 and Steps SC3 and SC4 for calculating the anesthetic depth $D_S$ based on the temperature difference S $(=T_{cent}-T_{dist})$, and the means 158 and Steps SC5 and SC6 for calculating the anesthetic depth $D_R$ based on the temperature ratio R $(=T_{cent}/T_{dist})$ are employed. However, one of the above-indicated two anesthetic depth determining devices may be omitted.

In the embodiment shown in FIG. 13, the anesthetic depths $D_S$ and $D_R$ are calculated on the basis of the temperature difference S $(=T_{cent}-T_{dist})$ and the temperature ratio R $(=T_{cent}/T_{dist})$, respectively. However, the temperature difference S $(=T_{cent}-T_{dist})$ or the temperature ratio R $(=T_{cent}/T_{dist})$ may be corrected or modified based on other parameters. In any case, the anesthetic depth $D_S$ or $D_R$ is calculated on the basis of the temperature difference S $(=T_{cent}-T_{dist})$ or the temperature ratio R $(=T_{cent}/T_{dist})$, respectively.

It is to be understood that the present invention may be embodied with other changes and modifications that may occur to those skilled in the art without departing from the scope of the invention.

INDUSTRIAL UTILITY

It is understood from the above description that since the anesthetic depth measuring apparatuses according to the present invention can quantitatively and objectively measure an anesthetic depth of a patient, they are suitable for use in an operating room, an intensive care unit, or the like where the patient is generally anesthetized.

We claim:

1. An anesthetic depth measuring apparatus for measuring an anesthetic depth of a living subject, characterized by comprising:

a pulse period measuring device which continuously measures a period of a pulse of the subject;

pulse period fluctuation signal extracting means for extracting, from a fluctuation of the pulse periods continuously measured by said pulse period measuring device, a first pulse period fluctuation signal which corresponds to a first pulse period fluctuation component produced in substantial synchronism with a respiration of the subject and a second pulse period fluctuation signal which corresponds to a second pulse period fluctuation component having a predetermined frequency lower than a frequency of the first pulse period fluctuation component; and anesthetic depth calculating means for calculating an anesthetic depth of the subject based on a ratio of said first pulse period fluctuation signal to said second pulse period fluctuation signal.

2. An anesthetic depth measuring apparatus according to claim 1, wherein said pulse period fluctuation signal extracting means extracts, as said first pulse period fluctuation signal, pulse period fluctuation components having frequencies in a predetermined frequency range including a frequency of the respiration of the subject.

3. An anesthetic depth measuring apparatus according to claim 1, wherein said pulse period fluctuation signal extracting means extracts, as said second pulse period fluctuation signal, pulse period fluctuation components having frequencies in a predetermined frequency range including a frequency of about one third to one fourth of a frequency of the respiration of the subject.

4. An anesthetic depth measuring apparatus for measuring an anesthetic depth of a living subject, characterized by comprising:

a pulse period measuring device which continuously measures a period of a pulse of the subject;

pulse period fluctuation signal extracting means for extracting, from a fluctuation of the pulse periods continuously measured by said pulse period measuring device, a first pulse period fluctuation signal which corresponds to a first pulse period fluctuation component produced in substantial synchronism with a respiration of the subject and a second pulse period fluctuation signal which corresponds to a second pulse period fluctuation component having a predetermined frequency lower than a frequency of the first pulse period fluctuation component;

first anesthetic depth calculating means for calculating a first anesthetic depth of the subject based on a ratio of said first pulse period fluctuation signal to said second pulse period fluctuation signal;

a blood pressure measuring device which continuously measures a blood pressure value of the subject;

blood pressure fluctuation signal extracting means for extracting, from a fluctuation of the blood pressure values continuously measured by said blood pressure measuring device, a blood pressure fluctuation signal which corresponds to a blood pressure fluctuation component having a predetermined frequency lower than a frequency of a respiration of the subject;

second anesthetic depth calculating means for calculating a second anesthetic depth of the subject based on a magnitude of said blood pressure fluctuation signal; and anesthetic depth determining means for determining a third anesthetic depth of the subject based on the first anesthetic depth calculated by said first anesthetic depth calculating means and the second anesthetic depth calculated by said second anesthetic depth calculating means, so that the determined third anesthetic depth is displayed on a display device.

* * * * *